(12) United States Patent
Saarela

(10) Patent No.: US 6,362,222 B1
(45) Date of Patent: Mar. 26, 2002

(54) ANALGESIC USE OF PODOPHYLLOTOXIN FOR TREATING PAIN CONDITIONS IN FEMALE GENITAL ORGANS

(76) Inventor: Eero Saarela, Keskussairaalantie 6 H 2, Savonlinna (FI), 57120

( * ) Notice: Subject to any disclaimer, the term of this patent is extended or adjusted under 35 U.S.C. 154(b) by 0 days.

(21) Appl. No.: 09/743,848

(22) PCT Filed: Jul. 16, 1999

(86) PCT No.: PCT/FI99/00632

§ 371 Date: Jan. 17, 2001

§ 102(e) Date: Jan. 17, 2001

(87) PCT Pub. No.: WO00/03708

PCT Pub. Date: Jan. 27, 2000

(30) Foreign Application Priority Data

Jul. 17, 1998 (FI) .................................................. 981632

(51) Int. Cl.[7] ...................... A61K 31/357; A61K 31/365
(52) U.S. Cl. ........................................ 514/463; 424/405
(58) Field of Search ....................... 514/463; 424/78.07, 424/430

(56) References Cited

U.S. PATENT DOCUMENTS 4,788,216 A   11/1988   Leander et al.

FOREIGN PATENT DOCUMENTS

| FI | 89330 | 6/1993 |
|----|-------|--------|
| FI | 100769 | 2/1998 |

OTHER PUBLICATIONS

Rothman K. F., Current Opinion in Pediatrics, 1995, 7, 415–422.*
W.A. Growdon et al., Pruritic vulvar squamos papillomatosis, Obstetrics and Gynecology, 1985, 564–568, vol. 66(4).
P. Broso et al., La vestibolite vulvare, Minerva Ginecologica, 1994, 109–114, vol. 46(3).

* cited by examiner

Primary Examiner—Edward J. Webman
Assistant Examiner—Helen Nguyen
(74) Attorney, Agent, or Firm—Rothwell, Figg, Ernst & Manbeck

(57) ABSTRACT

A method of treating a disease condition intermediated by a center of stimuli which regulates autonomic activity of an internal organ involves administration of an effective amount of podophyllotoxin.

3 Claims, No Drawings

ANALGESIC USE OF PODOPHYLLOTOXIN FOR TREATING PAIN CONDITIONS IN FEMALE GENITAL ORGANS

The invention relates to a new application of podophyllotoxin to topical pain relief in the treatment of pains in the genital organs, especially of vulvodynia and pains after hysterectomy.

There are several causes to pains in the female genital organs. Pains may be caused for instance by infections, tumours, circulatory disorders and various mechanical impacts. In addition to this, however, many other pains occur which cannot be explained by the factors above, all the findings being normal in examinations. Thus, for instance, a vaginal pain called vaginismus is known, which has always given a normal result in topical examination. For this reason, the pain has been considered psychogenic. A more recent denomination for a similar pain is vulvodynia, i.e. a vulvar pain for which no clinical cause can be found. The pain can be even invalidatingly strong, and it often starts suddenly as the result of an inflammation and may last for several years.

Various forms of vulvodyina are known. Vestibulitis is a finding called inflammation of the vulvar glands. In this condition, Bartholin's glands and both sides of the urethra and sometimes also the separate small glands (minor vestibular glands (gl.v.minor)) are very tender even to light palpation and still seem to be inflamed. Dysesthetic vulvodynia is otherwise identical, with the exception that the vulvar glands do not look inflamed at least macroscopically.

Since there is no overall theory for the causes of vulvodynia, there are very varied treatment, which have a very poor effect on the whole. Also, it is not obvious for physicians, not even gynecologist, to identify the condition. In fact, there have been many attempted ways of treating vulvodynia, with poor results.

The pain has assumably been caused by an inflammation in the vestibular glands, and the condition has consequently been treated as such. Various inflammatory agents have been searched with poor results. Antibiotics have not had any effect, nor have cortisone injections under the glands.

Topical pain relief has been tested by administering local anaesthetics either as injections or superficially, either in the entire vulva or under the sore glands. The results have been very unsatisfactory, and what is more, such a treatment involves the risk of allergy to anaesthetics. Systematic analgetic treatment has also been tested, however, opiates have been confirmed not to kill but rather to intensify the pain. Nor have prostaglandin suppressors relieved the pain. Among analgetics spasmolytics have proved useful in some cases, but only passingly, however.

Among antidepressants amitriptyline is probably the most frequently used and effective drug. Used for analgetic purposes it is effective in a smaller dose than used as an antidepressant. Nevertheless, this drug has bad general side effects and requires long-term treatment. No other antidepressants have been confirmed to be effective.

In the most severe cases of vulvodynia surgery is often used to remove a relatively large portion of the vulvar rear part at the line between the mucous membranes and the dermal areas. The large portion to be removed also includes Bartholin's glands. In the most severe cases, surgery helps fairly well (approx. 75%), however, it has a very invalidating effect. After surgery, vaginal humidification during intercourse is prevented. In addition, some patients still suffer from pains after the surgery, and they can hardly be offered any other treatment at all.

The description above shows that the treatment of pains in the genital organs of the type of vulvodynia is totally unsatisfactory with current techniques. The detection of the condition is perhaps additionally impaired by the absence of effective treatment and ignorance of the mechanism of the disease.

One sector of pains in the genital organs is a sore uterus, which is not considered a separate disease as such. It is treated with hysterectomy, which is often carried out because of some other diagnosis. In most cases, hysterectomy gives a distinct and permanent relief to the pain symptoms from which the patient suffers, and, in fact, the vagina is generally considered not to cause any sense of pain. Nevertheless, patients sometimes become very ill again after hysterectomy. They feel the pain in the lower abdomen, stronger on either side, and it may radiate to both flanks and to the back. It is often connected with urinary disorders, most often a need for urination, but also urinary incontinence and even cystitis.

There is no overall explanation to pains after hysterectomy. The most commonly used explanation is adhesion pains. The patient has relatively often been found to suffer from some kind of inflammatory symptoms, which develop pains after hysterectomy. The adhesions are sometimes searched by laparoscopy. Adhesions are either found or more often not found, and the treatment of found adhesions does not have any effect on the pain.

In young patients suffering from the pain endometriosis is a usual finding, which may sometimes provide an explanation to the pain. By contrast, it does not give an explanation to the pains in elderly, post-menopausal patients. The postoperative treatment of endometriosis is hormonal treatment, which does not relieve the pain, however.

Because of pains after removal of the ovaries, remaining ovarian tissue is sometimes searched in the region of the vaginal peak suspensions, and a pathologist may in fact find ovary-like tissue in the samples by careful searching. The pains may even subdue in some cases, which may be primarily due to the large section, and not to any ovarian tissue findings, which do not have any impact on successful pain relief.

Pains in the genital organs are often connected with urinary disorders, and since the urinary tracts run near the surgery region, the pains are assumably caused by these. The urinary tracts are very susceptible to pain and cause very strong pain for example in connection with cystolithiasis. However, there is no diagnostic test for stating pain in the urinary tracts nor for treating it. Patients who suffer from pain after hysterectomy under the diagnosis of ureter disorder are often transferred to some other speciality and are thus completely out of sight.

The present invention is based on the unexpected finding that podophyllotoxin topically administered has a very good effect on inexplicable pains in the genital organs. Podophyllotoxin is a previously known drug which has been used for local treatment of verrucae, especially condyloma.

The essential characteristics of the invention are defined in the accompanying claims.

The podophyllotoxic treatment of the invention can be generally applied to patients who suffer from pain in the lower abdomen and urinary disorders, for which no obvious reason can be found. The invention can be especially applied to the treatment of patients who suffer from inexplicable pains in the genital organs, i.e. vulvodynia. Usually these patients suffer from strong vulvar pain, for which no cause is found in a conventional gynecological examination. In accordance with the invention, podophyllotoxin can also be used in the treatment of patients with recurrent candidiasis.

The typical complaint of vulvodynia patients are pains during intercourse or other unspecific pains in the genital organs. Urinary disorders are common, and among these incontinence is a distinct separate symptom. Most of the incontinence disorders are mixed, i.e. prolapse is also connected with forced incontinence. Dysuria, i.e. an infection-like urinary disorder without bacteria is common. It may be impossible for the patient to remain sitting over long periods of time. Vaginal dryness is frequent as a separate symptom. Recurrent candidiasis is the sole symptom in some cases. This may be caused by a pathogenic fungus, however, a fungus-like symptom often occurs without any detectable fungus.

Unexpectedly, the patients themselves nor the physicians have not previously observed that the pain is specifically concentrated to the gland orifices. Yet it is commonly known that large vulvar palpation with a cotton-tipped applicator causes the strongest pain in clock directions 1, 5, 7 and 11, which coincide with Bartholin's glands and the uneven region of the sides of the urethra. Pain is also felt in directions 12 and 6, apparently because of radiation to both sides.

A post-hysterectomic pain which is relieved by applying podophyllotoxin on the sore vaginal peak corners can be categorised as a new disease on which there are no known publications. The pain may start at once after surgery or only after a number of years. Some kind of inflammatory symptoms may have occured after surgery. The pain starts rather suddenly, as does vulvodynia. Many patients have suffered from distinct vulvodynia before, from which they have recovered, however. The hysterectomy is often caused by various reasons, such as perhaps a sore uterus, however, since this is not sufficient as the sole reason for hysterectomy, surgery has been carried out for various other reasons, such as tumours or prolapse.

Post-hysterectomic pain is apparently also connected with other functional gastric disorders. The patients have often been largely treated and examined in other specialities. Disorders regarded as functional and possibly allergic or auto-immune diseases seem frequent.

So far, there is no theory whatsoever about the vulvodynia agents or causes, nor has any effective treatment of this been reported. It is also known that the uterus may be sore, but as the pain cannot be diagnostically stated, a sore uterus is not considered a separate disease. The potential causes of vulvodynia are explained below.

Vulvodynia (vulvar pain), a sore uterus (connected with various other findings) and post-hysterectomic pain are various forms of the same disease. They relate to a functional disorder of the birth canal, similar diseases of the other organs being, inter alia, migraine, asthma, irritable colon, prostatodynia. This complex of diseases has no name so far.

Post-hysterectomic pain for which no clinical cause is found is characterised by the fact that both corners of the vaginal peak are very tender to touch and hyperemia, haemorrhage or papillarity may be found. The pain is concentrated to these corners, but the whole vagina may be sore, and the pain radiates to the urinary tracts and the rectum. There may also occur a strong pain radiating from the lower abdomen towards the kidneys. Opiate and prostaglandin inhibitors do not relieve the pain.

The disease is apparently caused by a convulsion of a smooth muscle. There is always active smooth muscle tissue everywhere in the organism. Typical functions are, inter alia, peristaltis of the intestines and the urinary tracts and flexibility of the vascular system. The function of a smooth muscle may be congenitally defective (Prune Belly symptom in the urinary tracts and, inter alia, megacolon in the intestines).

Birth canal peristaltis occurs in the uterine tube. The labour procedure also represents peristaltis, and is subject to very careful and purposeful control. The control mechanism of the labour procedure is not very well known. *Uterus peristaltis* as an explanation, inter alia, to menstrual pains has been studied. Separate endometrium peristaltis has also been reported. The active function of the vaginal wall has not been studied in detail, its active function occurs as contractions during coitus and as transudation caused by activation of a muscular layer. The muscular contraction causes moisture penetration.

The function of the smooth muscular tissues is controlled by the autonomous nervous system by secreting to its immediate vicinity various transmitters, of which at least 100 different ones are known. The transmitters are common in the entire organism, and they have varying effects in different parts of the organism. The transmitters are assumed to be low-molecular in size and to decompose quickly in the organism. The receptor of many of them is known, and pharmaceuticals can be prepared to prevent this receptor effect. A separate effect mechanism is prevention of transmitter recovery (serotonin in depression), so that the substance once prepared by the organism is saved. The preparation of a transmitter is an energy-consuming operation, and thus a drop in the activity of the dopamine-preparing enzym causes parkinsonism. Drugs affecting the receptor substance synthesis are known.

Nevertheless, it has now been surprisingly found that pain in the genital organs can be treated with local podophyllotoxin application. Podophyllotoxin is known to confuse the tubular structures of the cells (tubular systems through which the cells secrete their transmitter). The effect site is the same as for the cancer medicine Taxol. Thus podophyllotoxin is considered to be a cytostatic. The former use of the substance in the treatment of condyloma is not based on its effect on the virus itself.

In connection with the present invention the effect of podophyllotoxin assumably is obvious long-term destruction of the tubular structures of the cell. The capacity of the cell to secrete its own transmitter is then impaired. It may be VIP (i.e. vasoactive intestinal peptide). Without this, there will be disorders in the renewal of the vascular system. The same effect is produced for instance by angiostatine, an anti-vascular growth substance of the organism, which is being studied in carcinoma treatment, because it prevents the blood circulation required for the tumour. The anti-vascular growth action explains why the ligulate growth of the mucous membrane caused by condyloma is prevented. The vascular build-up is a vital mechanism in condyloma growth.

When administered, podophyllotoxin has merely a local effect at the points of pain. In order to function adequately, the smooth muscular structures, the intestines, the veins, the birth canal and other parts of the organism require a control system. Peristaltis does not function as such, but the organism needs some kind of central command system in its epithelium. The autonomous nervous system, the (sympathetic and parasympathetic) nerves do not carry out activity in practice, they only perform control. Their effect and, at the same time the sensations, pass through the control centre.

Bartholin's glands are approx. ½ cm deep recesses outside the labia minor at the vaginal entry, within the mucous membrane area. In healthy persons, they can be seen with colposcopy as an approx. 1 mm orifice which is filled with a transparent mucus. The gland may show a slow, periodical contraction. At palpitation there is a sensation but no pain in the gland. Sometimes the gland orifice is closed and the gland secretion grows a cyst, which may remain for several years and become inflamed in some cases. If the glands are removed for some reason, e.g. for the treatment of vulvodynia, this will result in vaginal dryness.

Apparently Bartholin's glands act as a local centre of stimuli closely connected with intercourse. I find Bartholin's gland to be somehow disturbed, over-active as a centre of stimuli in vulvodynia. The central nervous system senses the over-stimuli as a pain, and the susceptibility to pain of the centre of stimuli is explicitly a clear symptom of a disorder. The disorder is also connected with an over-active function, resulting in an increase in the required blood circulation, which appears as redness the gland. The change has the same aspect as an inflammation. However, there is no inflammation of the irritated gland. Cortisone or antibiotics do not relieve the pain. Nor do prostaglandin inhibitors, and hence there is no inflammation.

It can be assumed that Bartholin's glands have no external secretion activity, but act as coordinators of the smooth muscular peristaltic function in the birth canal. Bartholin's glands are over-activated by som external cause, and the stimuli cycle continues. The continuous stimulus is connected with an active cell proliferation, which sometimes appears as a crater-like growth of the gland edges and a ligulate aspect. This active function requires increased circulation, which is also visible. The effect of podophyllotoxin is based on a decrease in blood circulation. The podophyllin treatment does not kill the pain at once, but on the contrary, increases the pain. Apparently the exhaustion of cell reserves and slow transmitter elimination release the relief of the sense of pain only in the course of a couple of weeks.

There are recesses with varying aspects, often netlike, on the sides of the urethra. These glands are not Skene's glands. These separate, actively functioning organs have no name of their own. In conjunction with this invention, they are assumed to be centres of stimuli similar to Bartholin's glands. Their function is primarily to permit urination. Like Bartholin's glands, they seem to act as control centres in closing the genital canal. The action of the autonomous nervous system is transmitted through these, in this case as the urination process. A disorder in their function is often similar to that of Bartholin's glands, and often simultaneous with this. A simultaneous disorder of these two would be a good explanation to why vulvodynia and urinary disorders occur simultaneously and are hard to understand.

In a condition of vestibulitis type small cavities with a diameter of approx. 1 mm are often visible on the mucous membranes of the front part of the vulva, the cavities being red, visible to the eye and very tender to touch. These changes are centres of stimuli, sub-centres, whose activity has resulted in proliferation. Pain at these points is also relieved with podophyllin treatment.

Stimuli centres in the smooth muscular tissues are probably not exclusively a gynecological phenomenon. On the whole, the function of a smooth muscle cannot occur at random and only locally, but assumably there are similar centres of stimuli everywhere in the organism, which simultaneously act as sensory receptors of the autonomous nervous system.

Regarding post-hysterectomic pain the theory of a centre of stimuli described above is explained by the fact that separate centres of stimuli develop at the upper corners of the vagina. It is a fact that the vagina functions normally after hysterectomy. The vaginal corners have always been susceptible to the growth of cheloids, which have been very sore and hyperemic. Before hysterectomy the centres of stimuli are probably located in the are a of the cervix. They may sometimes result in a sore cervix after uterus amputation.

The fact that the pain is relieved in a post-hysterectomic situation with local podophyllotoxin treatment in the same way as in vulvodynia confirms the idea of the recovery mechanism of vulvodynia. It also confirms the theory of certain centres of stimuli.

In the treatment, the vagina is first washed with a 3% acetum solution. The vulva, especially Batrholin's glands are examined by means of colposcopy. A second object is a slightly uneven, netlike area located obliquely behind, at the sides of the outer mouth of the urethra. Sometimes small hyperemetic cavities, small vestibular glands are found in the vulvar region, which are not sore in a healthy person. In vulvodynia they are typically very tender to touch and red, ligulate and with embossed edges. In vulvodynia Bartholin's gland orifices are sometimes closed. These points often start bleeding at palpation.

In accordance with the invention, the sore glands are pencilled with podophyllotoxin. Any commonly used vaginal ointment is applied on the pencilled area. The treatment is repeated twice if necessary at an interval of about one month. The treatment is usually not effective at once, however, in the course of typically two weeks there is no more pain.

In accordance with the invention podophyllotoxin can also be used for intense tenderness to touch and palpation in the upper vaginal corners with post-hysterectomic pain, sometimes also with bleed in. After the rinse with acetum the vaginal corners are treated with podophyllotoxin, and vaginal ointment can be applied on the treated areas if necessary. The treatment can be repeated at least three times if necessary, at intervals of either one day or one month. The results are extremely good.

Podophyllotoxin can be used as such or mixed with a carrier or a filler to form a pharmaceutical preparation suitable for topical administration.

The invention is described below by means of examples.

EXAMPLE 1

In a patient who complained about pain during intercourse an examination by means of colposcopy showed both Bartholin's gland orifices to be papillary, bleeding and very tender to touch. The gland orifices were pencilled with a 5% podophyllotoxin solution. The pain during intercourse disappeared at the end of a couple of weeks. After about two years the pain recurred. Podophyllotoxin was applied to the gland orifices anew. At the end of two months the lefthand, still tender gland orifice was pencilled once more. After this, the pain disappeared completely in the course of a couple of weeks.

EXAMPLE 2

The patient had undergone hysterectomy because of prolapse and extended cervix. However, the prolapse recurred (enterocele), and was resectioned from below. After the surgery the patient suffered from vaginal pain, which was stronger on the left side. There was no inflammation, the pain persisted. A gynecologist made repeated examinations, found nothing wrong and consulted a neurologist, who made the diagnosis inexplicable postoperative pain. The examination showed that the left Bartholin's gland and the right side of the urethra were red and very tender to palpation. Podophyllotoxin was applied twice at one month's interval and once more the following day. After this the patient was free of symptoms.

At the end of about three years the patient returned to the gynecologic outpatient clinic and complained about a strong continual pain in the lower part of the abdomen and a pushing feeling in the rectum. The gynecologist found that the vulva was clean, no recurrent prolapse, touch per rectum normal, dryness in the mucous membranes. The vaginal peaks were treated locally with podophyllotoxin three times at two days' intervals. Especially the right corner was very tender to palpation. After the third treatment there was no more pain.

EXAMPLE 3

The patient hade undergone hysterectomy, suffered from pain, a small muscular tumour and adhesions after endometriosis. The patient had suffered from incontinence for about a year. There had been no distinct inflammations. The sore glands in the introitus were pencilled with podophyllotoxin once, and after one month there was no pain in the glands, but the vaginal peaks were still very tender to palpation. They were pencilled. Nevertheless, after about six months the patient returned to the clinic because of pain in the lower abdomen, the back and a sting in the urinary bladder. The sore vaginal peaks were pencilled with podophyllotoxin once more. At the control one month later the patient declared herself to be completely recovered and the incontinence had also disappeared.

EXAMPLE 4

A total of 151 patients were treated over a period of two years, and among these 75% had typical vulvodynia symptoms and the remainder atypical other symptoms, such as disorders of the urinary tracts, vaginal dryness, itching and recurrent candidosis. However, intense tenderness to touch of the vestibular glands was typical for all of the patients.

All of the patients were treated in the same way: first the vagina was washed with a 3% solution of acetum, the sore glands were treated with podophyllotoxin and vaginal ointment was applied on this. 46 patients were treated only once and 6 patients were treated 10 times, the patients were treated 2.6 times on the average.

About two weeks after the treatment, about one hundred patients were found to be free of symptoms. 40 patients were considered to have probably recovered, and part of them were completely free of symptoms later, with a maximum follow-up period of more than 5 years.

EXAMPLE 5

Post-hysterectomic pain was examined in 26 patients. The vagina was first washed with a 3% acetum solution and then the vaginal peaks were pencilled with podophyllotoxin. A vaginal ointment was used occasionally on the pencilled areas. The treatment was repeated 1 to 3 times at about one month's intervals.

17 patients remained free of symptoms during the control period. The maximum control period was 9 months.

For nine of the patients the treatment has not yet been completed. Part of them have had only limited symptoms, and part of them, who have had the opportunity of further treatment, have not showed up, in other words, the symptoms have apparently disappeared with the earlier treatment cycles.

In half of these patients, vulvodynia had been earlier discovered and treated to be symptomless. The fact that both these disorders occur in the same patients and that they are cured with the same method of treatment implies that they are different forms of the same disease, i.e. a functional convulsive pain in the birth canal.

What is claimed is:

1. A method of treatment of pain associated with vestibulitis, candidiasis, or a urinary tract disorder, comprising topically administering an effective amount of pdophyllotoxin so as to treat said pain.

2. The method of claim 1 wherein said urinary tract disorder is incontinence, forced inontinence or dysuria.

3. A method of treatment of pain associated with a genital organ, wherein said pain in said genital organ is vulvodynia, posthysterectomic pain or uterus pain.

* * * * *